United States Patent
Marechal et al.

(10) Patent No.: US 7,063,864 B1
(45) Date of Patent: Jun. 20, 2006

(54) MORPHINE SULPHATE MICROGRANULES, METHOD FOR PREPARING SAME AND COMPOSITIONS CONTAINING SAME

(75) Inventors: Dominique Marechal, Dreux (FR); Pascal Suplie, Montaure (FR); Pascal Oury, Le Chesnay (FR)

(73) Assignee: Laboratoires des Products Ethiques Ethypharm, Houdan (FR)

( * ) Notice: Subject to any disclaimer, the term of this patent is extended or adjusted under 35 U.S.C. 154(b) by 337 days.

(21) Appl. No.: 10/009,341

(22) PCT Filed: Jun. 8, 2000

(86) PCT No.: PCT/FR00/01573

§ 371 (c)(1),
(2), (4) Date: Jun. 19, 2002

(87) PCT Pub. No.: WO00/74659

PCT Pub. Date: Dec. 14, 2000

(30) Foreign Application Priority Data

Jun. 9, 1999 (FR) .................................. 99 07259

(51) Int. Cl.
*A61K 9/14* (2006.01)
*A61K 9/16* (2006.01)

(52) U.S. Cl. ........................ 424/490; 424/489
(58) Field of Classification Search ................ 424/489, 424/490

See application file for complete search history.

(56) References Cited

U.S. PATENT DOCUMENTS

| | | | |
|---|---|---|---|
| 5,445,829 A | 8/1995 | Paradissis et al. | |
| 5,672,360 A * | 9/1997 | Sackler et al. | 424/490 |
| 6,077,544 A | 6/2000 | Debregeas et al. | |

FOREIGN PATENT DOCUMENTS

| EP | 0 205 282 A2 | 5/1986 |
|---|---|---|
| EP | 0 609/961 A1 | 1/1990 |
| EP | 0 377 518 | 7/1990 |
| EP | 0 553 392 A1 | 8/1992 |
| EP | 0636 366 A2 | 7/1994 |
| EP | 0 647 448 | 4/1995 |
| FR | 2 771 291 | 5/1999 |
| WO | WO 94/22431 A1 | 10/1994 |
| WO | WO 95/31972 A1 | 11/1995 |
| WO | WO 96/00066 A1 | 1/1996 |
| WO | WO 96/14059 A1 | 5/1996 |

* cited by examiner

*Primary Examiner*—Thurman K. Page
*Assistant Examiner*—Humera N. Sheikh
(74) *Attorney, Agent, or Firm*—Foley & Lardner LLP

(57) ABSTRACT

The present invention concerns a novel sustained-release oral formulation of morphine sulphate in the form of microgranules. Each microgranule comprises a neutral support grain coated with an active layer and with a sustained-release layer, characterized in that the sustained-release layer contains a copolymer of methacrylic acid and of methyl methacrylate ester, the relative proportion of the free carboxyl groups and of the ester groups of which is equal to 0.5 approximately, and a silica exhibiting a hydrophobic character. The present invention also concerns a process for preparing these microgranules which is carried out entirely in aqueous medium by emplacing on neutral support grains.

16 Claims, 1 Drawing Sheet

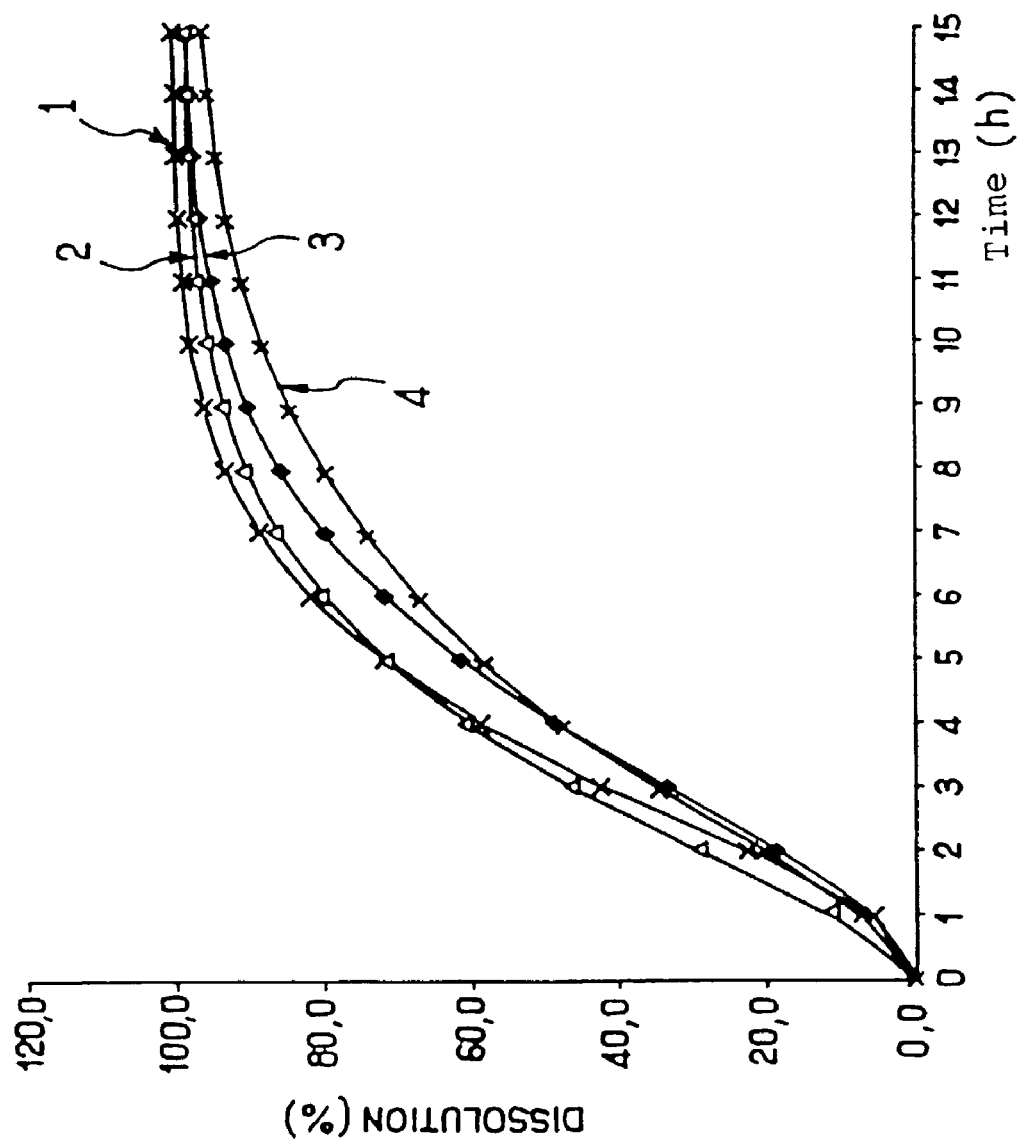

MORPHINE SULPHATE MICROGRANULES, METHOD FOR PREPARING SAME AND COMPOSITIONS CONTAINING SAME

The present invention concerns a novel sustained-release morphine sulphate formulation for oral administration.

The present invention also applies to the process for manufacturing this formulation and to the pharmaceutical preparations containing it.

In the present application, "morphine sulphate" is intended to mean the sulphate salt, optionally hydrated, of (5 alpha, 6 alpha)-7,8-didehydro-4,5-epoxy-17-methylmorphinane-3,6-diol.

The oral administration of morphine sulphate is the best suited treatment for relieving chronic pain. Many oral formulations of morphine sulphate have been described in the prior art.

EP 205 282 (EUROCELTIQUE) relates to granules comprising morphine sulphate, an aliphatic alcohol and a water-soluble hydroxyalkylcellulose.

These granules are coated with a derivative of mucoadhesive cellulose, such as hydroxypropylmethyl-cellulose, and present a release profile over 12 hours, with a plasmatic peak situated between 1 and 3 hours.

EP 377 518 (FAULDING) discloses sustained-release granules containing a very water-soluble active principle such as morphine. The granules make it possible to maintain plasmatic levels higher than 75% of the maximum for at least 3 hours.

These granules comprise an active core coated with a polymeric layer which allows a slow release of the active principle at a very acid pH and a constant faster release of the active principle at a pH which is less acid to basic, over an extended period of time.

This polymeric layer contains three compounds: a polymeric matrix which is insoluble whatever the pH, an enteric polymer, the solubility of which is pH-dependent, and a polymer which is soluble in acid medium.

The preparations described in EP 377 518 have a bioavailability requiring an administration which should be at least twice daily.

A subject of EP 553 392 (EUROCELTIQUE) is a process for preparing a stable sustained-release formulation consisting of granules obtained in a fluidized air bed by spraying an aqueous solution of active principle over neutral grains, followed by a coating with HPMC, by a coating with an acrylic polymer and by a protective film required for reducing the agglomeration of the granules.

EP 636 366 (EUROCELTIQUE) discloses sustained-release morphine sulphate microgranules comprising a neutral core coated with an active layer consisting of an active principle/HPMC mixture, of a sustained-release layer consisting of Eudragit® RS D and/or of Eudragit® RL D, and of an HPMC film, which represents 5% of gain in mass.

In documents EP 533 392 and EP 636 366, the granules undergo a heat treatment above the glass transition temperature of the polymeric coating, in order to stabilize its structure. This heat treatment is carried out at 45° C. approximately for at least 24 hours, which considerably lengthens the duration of the process.

EP 647 448 (EUROCELTIQUE) discloses morphine sulphate granules, the in vitro dissolution profile of which stretches over 24 hours. The granules consist of Neutral grains coated with active principle and with lactose. The active layer is covered with a film of Opadry®, and then coated with Aquacoat ECD 30®, Eudragit RS 30 D® or a Eudragit RS®/Eudragit RL® mixture: 97.5/2.5. The titre of the granules described in this document is quite low, of the order of 15%.

U.S. Pat. No. 5,445,829 (KV Pharmaceutical) relates to a formulation which is capable of releasing the active principle exclusively between 12 and 24 hours after the administration.

This formulation contains 0 to 50% of immediate particles and the complement of controlled-release particles consisting of immediate particles coated with a cellulose derivative as delaying polymer.

WO 94/22431 (KAPIPHARMACIA) discloses a controlled-release formulation of a morphine salt.

This formulation can be administered in a single daily dosage intake. At 32 hours, the plasma concentration is higher than Cmax/2 and the fluctuations in the release profile are very small over this period, and so the plasmatic concentration is virtually constant over 24 hours.

The formulation disclosed in WO 94/22431 consists, for example, of granules containing a core of morphine salt, of lactose and of a binder, coated with a film of HPMC/EC and of triethyl citrate.

This formulation uses a mixture of two polymers, one being soluble and the other being insoluble in water.

WO 95/31972 (EUROCELTIQUE) discloses sustained-release morphine sulphate granules consisting of a neutral core coated with active principle and with hydrated lactose, the bulk density of which is between 0.4 and 0.9 g/ml. The delayed-release layer coating the active principle contains for example an acrylic polymer, an alkylcellulose, a hydrogenated vegetable oil or a mixture thereof.

This document teaches that the binding of the morphine sulphate to the neutral cores requires the addition of the lactose as a diluent.

The release profiles of the microgranules given by way of example show that these granules are suitable for one dosage intake per day.

WO 96/14059 (EUROCELTIQUE) discloses a process for extruding spherical particles containing morphine sulphate, a support the melting point of which is between 35 and 150° C. and a sustained-release agent.

The support is a hydrogenated vegetable oil or a PEG (Mw 1000 to 20,000). The in vitro dissolution profile of these particles is 67% at 24 hours. No in vitro result is provided.

WO/960066 (ALZA) describes a composition containing morphine sulphate, polyvinylpyrrolidone and a polyalkylene oxide.

This document claims that the formulation provides a sustained release over time, but gives no example either in vitro or in vivo, and so it is difficult, upon reading the document, to estimate whether the administration should be one or more dosage intakes per day.

The subject of the present invention concerns sustained-release morphine sulphate microgranules each comprising a neutral support grain coated with an active layer and with a sustained-release layer, characterized in that the sustained-release layer contains a copolymer of methacrylic acid and of methyl methacrylate ester, the relative proportion of the free carboxyl groups and of the ester groups of which is equal to 0.5 approximately, and a silica exhibiting a hydrophobic nature.

The hydrophobic silica represents advantageously 0.2 to 1% by weight of the micro-granules. Aerosil® R 972 is preferred as hydrophobic silica.

The microgranules of the invention exhibit in particular the advantage of lacking a protective film coating the sustained-release layer. In addition, it is not necessary to subject the microgranules to a very lengthy heat treatment (longer than 24 hours) as in the prior art to improve the structure of the sustained-release layer.

The acrylic copolymer represents advantageously 5 to 15% by weight of the microgranules.

The relative mass proportion of the morphine sulphate and of the neutral support grain is preferably between 40/60 and 60/40.

The morphine sulphate represents advantageously 30 to 40% by mass of the microgranules.

The neutral support grain coated with the active layer contains preferably 40% to 50% of morphine sulphate and 10 to 20% of a pharmaceutically acceptable binder.

The sustained-release layer contains preferably a plasticizer and a lubricant. The plasticizer and the lubricant are chosen from the pharmaceutically acceptable plasticizers and lubricants which are well known to persons skilled in the art. The plasticizer is for example triethylcitrate.

The composition of the microgranules according to the invention is advantageously as follows:
Morphine sulphate 30–40%
Neutral support grain 30–40%
Binder 10–20%
Methacrylic acid copolymer 5–15%
Plasticizer 1–2.5%
Lubricant 2–4%
Hydrophobic silica 0.2–1%
The neutral support grains have a particle size of between 200 and 1000 μm, preferably of between 400 and 600 μm.

The present invention also concerns a process for preparing the microgranules described above. This process is carried out entirely in aqueous medium. It comprises a step of emplacing, in aqueous solution, the active principle on neutral support grains and a step of coating with a methacrylic copolymer, still in aqueous solution.

The granules are advantageously prepared in a perforated rotary turbomixer or a fluidized air bed. The spraying of the emplacing and coating solutions and/or suspensions is preferably continuous and followed by a drying step at a temperature of between 30 and 65° C.

It is not necessary for the granules according to the invention to undergo a heat treatment for the structure of the film to be satisfactory.

The present invention finally concerns the pharmaceutical compositions containing the microgranules of the invention optionally obtained according to the process described above.

The following examples illustrate the invention without limiting the scope thereof.

The percentages are expressed by weight.

THE BEIEF DESCRIPTION OF THE DRAWINGS

The FIGURE represents the mean of the in vitro dissolution profile of four formulations according to the invention (curves 1, 2, 3 and 4). The percentage of dissolution is on the x-axis and the time (hours) on the y-axis.

Example 1

Batch A

Preparation of the Granules

An emplacing solution containing 74.7% of purified water, 6.6% of Pharmacoat 603® (hydroxy-propylmethylcellulose) and 18.7% of morphine sulphate is prepared. Stirring is maintained until the solution is homogeneous, and then throughout the emplacing.

Neutral support grains (400 to 600 μm) are placed in a rotating perforated turbomixer. The emplacing of the active principle on the neutral grains is carried out by continuous spraying of the emplacing solution described above, with a support of hot air at a temperature of between 35 and 60° C.

The mass of the active microgranules obtained is sieved through a screen of mesh size ranging from 0.71 to 0.85 mm.

A coating solution is prepared by successively adding Eudragit® RS 30 D (methacrylic acid copolymer), triethyl citrate, talc and Aerosil® R 972 (hydrophobic silica) to the purified water. The chemical name of Eudragit® RS 30 D is poly(ethyl acrylate, methyl methyacrylate, trimethylammonioethyl methacrylate chloride) 1:2:0.1. Stirring of the suspension is maintained until the mixture is homogeneous, and then throughout the coating.

The active microgranules are placed in a rotating perforated turbomixer and continuously sprayed with the coating suspension described above, at a temperature of 30° C. The mass of microgranules obtained is sieved through a screen of mesh size ranging from 0.8 to 1 mm.

This step can be repeated one or more times. The granules are then lubricated with an amount of talc which is equivalent to 0.5% of the coated mass obtained.

The microgranules obtained have the following composition:

|  | Batch A | |
|---|---|---|
|  | Amount mg | % by mass |
| Morphine sulphate | 12.5 | 37.3 |
| Neutral grains | 12.5 | 37.3 |
| Pharmacoat 603 ® | 4.4 | 13.0 |
| Eudragit RS 30 D ® | 2.7 | 8.2 |
| Triethylcitrate | 0.5 | 1.6 |
| Talc | 0.7 | 2.1 |
| Aerosil R972 ® | 0.1 | 0.4 |
| Content (mg/g) | 371 | |

In Vitro Dissolution Tests

The previously obtained microgranules are dissolved in 500 ml of water at 37° C. in a machine with paddles revolving at 100 revolutions/min. The U.V. absorbance reading is measured at two wavelengths, 285 nm and 310 nm.

| | Batch A | | | | | | | | | | | |
|---|---|---|---|---|---|---|---|---|---|---|---|---|
| Time (hours) | 1 | 2 | 3 | 4 | 5 | 6 | 7 | 8 | 9 | 10 | 15 | 20 |
| Percentage of dissolution | 6.6 | 20.8 | 38.8 | 55.8 | 69.9 | 79.9 | 86.3 | 90.7 | 93.2 | 94.8 | 97.8 | 98.3 |

The in vitro dissolution profile of Batch A is represented by Curve 3 of the FIGURE.

Tests for Stability of the Gelatin Capsules of Microgranules (Batch A1)

The stability properties of the microgranules which have been previously obtained and packaged in size 3 gelatin capsules each containing 60 mg of morphine sulphate are measured under storage conditions of at 25° C. and 60% relative humidity, for 24 months.

It is observed that the water content of the microgranules is stable at 6% on average, that the appearance of the gelatin capsules is satisfactory and that the active principle titre is in compliance and homogeneous.

The dissolution profiles are fairly stable over time.

After 24 months, the content of pseudomorphine and ampomorphine impurities is in compliance with standards (i.e. less than 05%).

The stability of the same gelatin capsules is also studied for 6 months at 40° C. and 75% relative humidity.

It is observed that the active principle titre is in compliance and homogeneous. The dissolution is stable at 6 months. Moreover, the water content is stable.

The stability results are presented in the following tables.

| Percentage of dissolution in vitro (Batch A1) Storage conditions 25° C., 60% RH | | | | | | | | |
|---|---|---|---|---|---|---|---|---|
| Hours | T 0 | 1 M | 3 M | 6 M | 9 M | 12 M | 18 M | 24 M |
| 1 | 7.8 | 7.4 | 7.7 | 7.1 | 6.1 | 6.5 | 6.4 | 5.5 |
| 2 | 21.6 | 21.9 | 23.2 | 22.4 | 18.9 | 19.7 | 20.1 | 17.0 |
| 4 | 55.2 | 57.3 | 60.2 | 58.1 | 52.7 | 53.1 | 52.9 | 50.6 |
| 6 | 78.9 | 81.7 | 83.7 | 81.0 | 77.8 | 76.1 | 73.4 | 76.1 |
| 8 | 89.9 | 93.4 | 93.8 | 90.8 | 90.1 | 86.7 | 81.9 | 88.5 |
| 12 | 96.0 | 100.2 | 98.8 | 95.9 | 97.5 | 93.0 | 86.2 | 95.4 |
| 16 | 96.4 | 100.6 | 99.8 | 96.9 | 98.7 | 94.6 | 86.9 | 95.4 |

| Percentage of dissolution in vitro (Batch A1) Storage conditions 40° C., 75% RH | | | | | |
|---|---|---|---|---|---|
| Hours | T0 | 1M | 2M | 3M | 6M |
| 1 | 7.8 | 6.0 | 5.9 | 6.1 | 6.3 |
| 2 | 21.6 | 19.8 | 19.7 | 19.7 | 21.0 |
| 4 | 55.2 | 57.1 | 57.3 | 57.0 | 58.7 |
| 6 | 78.9 | 83.1 | 81.8 | 81.9 | 83.2 |
| 8 | 89.9 | 94.3 | 92.1 | 92.9 | 94.0 |
| 12 | 96.0 | 100.1 | 97.5 | 98.7 | 100.3 |
| 16 | 96.4 | 101.5 | 98.0 | 99.6 | 102.4 |

| Active principle content (Batch A1) | | | | | | | | | | |
|---|---|---|---|---|---|---|---|---|---|---|
| | | T 0 | 1 M | 2 M | 3 M | 6 M | 9 M | 12 M | 18 M | 24 M |
| 25° C., 60% RH | mg/gelatin capsule | 59.0 | 58.4 | — | 56.7 | 59.3 | 58.1 | 58.0 | 57.6 | 57.0 |
| | Variation in % | — | −1.0 | — | −3.9 | 0.5 | −1.5 | −1.7 | −2.4 | −3.4 |
| 40° C., 75% RH | mg/gelatin capsule | 59.0 | 57.4 | 58.7 | 57.5 | 58.4 | — | — | — | — |
| | Variation in % | 0 | 2.7 | −0.5 | −2.5 | −1.0 | — | — | — | — |

| Water content (Karl Fisher) (Batch A1) | | | | | | | | | |
|---|---|---|---|---|---|---|---|---|---|
| | T 0 | 1 M | 2 M | 3 M | 6 M | 9 M | 12 M | 18 M | 24 M |
| 25° C., 60% RH | 6.1% | 5.9% | — | 5.9% | 6.1% | 4.8% | 6.1% | 6.1% | 5.9% |
| 40° C., 75% RH | 6.1% | 6.6% | 6.0% | 5.3% | 6.8% | — | — | — | — |

Pharmacokinetic Study No. 1.

The bioavailability of gelatin capsules of Batch A1 is compared to that of a reference morphine formulation (containing a dose of 30 mg), after 7-day repeated dose administration in 24 healthy volunteers.

| | Plasmatic concentration of | | | |
|---|---|---|---|---|
| | morphine | | 6 (glucuronide) morphine | |
| | Gelatine capsules of microgranules (Batch A1) 60 mg | Reference (Batch S 1079) 30 mg | Gelatin capsules of microgranules (Batch A1) 60 mg | Reference (Batch S 1079) 30 mg |
| $C_{max}$ (ng/ml)* | 18.3 | 12.8 | 77.6 | 59.2 |
| $C_{min}$ (ng/ml)** | 7.9 | 6.8 | 31.0 | 30.4 |
| $T_{max}$ (h)* | 5 | 5 | 6 | 3 |

*means
**medians

It is noticed that at Day 7, the plasmatic concentrations of morphine from the gelatin capsules of the invention at 24 hours are higher than the plasmatic concentrations from the reference at 12 hours (+1.1 ng/ml), which is a sign of good cover over 24 hours.

Pharmacokinetic Study No. 2

The bioavailability of gelatin capsules of Batch A1 is compared to that of a reference morphine formulation, after administration of a single dose of 60 mg in healthy volunteers.

The gelatin capsules of Batch A2 are of size 3 and contain a dose of 60 mg of morphine sulphate per gelatin capsule.

|  | Plasmatic concentration of | | | |
| --- | --- | --- | --- | --- |
|  | morphine | | 6 (glucuronide) morphine | |
|  | Gelatine capsules of microgranules of the invention (Batch A2) | Reference of the prior art (Batch S 1055) | Gelatin capsules of microgranules of the invention (Batch A2) | Reference of the prior art (Batch S 1055) |
| $C_{max}$ (ng/ml)* | 6.97 | 13.16 | 64.0 | 114.8 |
| $C_{min}$ (ng/ml)** | 6.0 | 2.0 | 5.0 | 3.0 |
| $T_{max}$ (h)* | 218.9 | 186.9 | 1471.49 | 1536.5 |

*means
**medians

The formulation of the invention and the reference are bioequivalent over the area under the curve parameters, which demonstrates an equivalent absorption of both products. Conversely, the release profile of the formulation of the invention appears more delayed than the reference, with a later $T_{max}$ and a lower $C_{max}$.

EXAMPLE 2

Batches B, C and D

Preparation of the Granules

Granules of the following composition are prepared according to the protocol of Example 1.

|  | Batch B | | Batch C | | Batch D | |
| --- | --- | --- | --- | --- | --- | --- |
|  | Amount (kg) | % by mass | Amount (kg) | % by mass | Amount (kg) | % by mass |
| Morphine sulphate | 13.7 | 35.1 | 31.0 | 40.9 | 728.8 | 41.9 |
| Neutral grains | 15.4 | 39.7 | 26.0 | 34.3 | 573.7 | 33.0 |
| Pharmacoat 603 ® | 4.8 | 12.3 | 10.8 | 14.3 | 204.1 | 11.7 |
| PEG 4000 | — | — | — | — | 51.0 | 2.9 |
| Eudragit RS 30 D ® | 3.2 | 8.2 | 5.1 | 6.7 | 126.5 | 7.3 |
| Triethylcitrate | 0.6 | 1.6 | 1.0 | 1.3 | 24.9 | 1.4 |
| Talc | 1.0 | 2.6 | 1.7 | 2.2 | 24.9 | 1.4 |
| Aerosil ® | 0.1 | 0.40 | 0.2 | 0.3 | 6.2 | 0.4 |
| Content (mg/g) | 371.3 | | 368.5 | | 397.9 | |

Batch B is prepared as in Example 1 in a Glatt perforated turbomixer, whereas Batches C and D are respectively prepared in an O'Hara perforated turbomixer or in a Laf Huttlin.

Tests for In Vitro Dissolution of the Microgranules

| Time (h) | | 1 | 2 | 3 | 4 | 5 | 6 | 7 | 8 | 9 | 10 | 15 | 20 | 24 |
| --- | --- | --- | --- | --- | --- | --- | --- | --- | --- | --- | --- | --- | --- | --- |
| % of dissolution | Batch B | 11.0 | 29.0 | 46.2 | 60.4 | 71.5 | 79.9 | 86.0 | 90.3 | 93.4 | 95.5 | 98.7 | — | — |
|  | Batch C | 5.3 | 22.2 | 42.1 | 58.5 | 71.6 | 81.6 | 88.5 | 93.0 | 95.9 | 97.8 | 100.4 | — | — |
|  | Batch D | 7.1 | 20.2 | 34.8 | 47.9 | 58.7 | 67.4 | 74.5 | 80.2 | 85.0 | 88.7 | 97 | 99.6 | 100.5 |

The in vitro dissolution profiles of Batches B, C and D are represented by curves 2, 1 and 4, respectively, of the FIGURE.

Tests for Dissolution of the Gelatin Capsules of Microgranules

The gelatin capsules of Batches B2, B1, D1 and C1 contain a dose of 60 mg of morphine sulphate.

| Time (h) | | 1 | 2 | 3 | 4 | 5 | 6 | 8 | 10 | 12 | 14 |
| --- | --- | --- | --- | --- | --- | --- | --- | --- | --- | --- | --- |
| % dissolution | Batch B1 | 15.2 | 34.1 | 51.1 | 64.8 | 75.3 | 83.2 | 93.3 | — | 100.4 | — |
|  | Batch C1 | 6.5 | 24.1 | — | 60.3 | — | 81.9 | 92.2 | 96.3 | 97.4 | 98.5 |

Tests for Stability at 25° C., 60% RH of Gelatin Capsule Batch B2 (Microgranules of Batch B)

|  | T 0 | 15 D | 1 M | 2 M | 3 M | 6 M |
|---|---|---|---|---|---|---|
| Water content (%) | — | 5.50% | 6.00% | 6.16% | 6.00% | 6.02% |
| Dissolution (hours) | | | | | | |
| 1 | 21.2 | 19.2 | 14.7 | 6.9 | 15.6 | 16.6 |
| 2 | 45.1 | 43.1 | 29.5 | 22.1 | 35.7 | 37.9 |
| 3 | 63.5 | 62.0 | 42.9 | 36.7 | 53.3 | 55.8 |
| 4 | 76.1 | 75.7 | 54.4 | 49.4 | 67.1 | 69.3 |
| 5 | 85.2 | 85.2 | 64.0 | 60.1 | 77.3 | 79.3 |
| 6 | 91.3 | 91.6 | 71.9 | 68.8 | 84.8 | 86.5 |
| 7 | 95.5 | 95.7 | 78.2 | 76.0 | 90.3 | 91.5 |
| 8 | 98.2 | 98.4 | 83.6 | 81.5 | 94.1 | 95.0 |
| 12 | 102.2 | 102.9 | 96.3 | 93.1 | 101.2 | 101.0 |

Tests for Stability at 40° C., 75% RH of Gelatin Capsules Batch D1 (Microgranules of Batch D)

|  | T 0 | 15 D | 1 M | 2 M | 3 M | 6 M |
|---|---|---|---|---|---|---|
| Water content (%) | 6.19% | 6.40% | 6.29% | 6.20% | 6.30% | 6.38% |
| Dissolution (hours) | | | | | | |
| 1 | 11.8 | 11.9 | 12.2 | 12.6 | 11.6 | 12.5 |
| 2 | 28.7 | 28.7 | 31.0 | 33.1 | 31.6 | 34.3 |
| 3 | 45.8 | 45.2 | 48.1 | 50.6 | 49.1 | 51.8 |
| 4 | 59.3 | 58.4 | 61.2 | 63.9 | 62.5 | 64.9 |
| 5 | 69.8 | 68.8 | 71.5 | 74.1 | 72.8 | 75.2 |
| 6 | 77.9 | 77.1 | 79.6 | 82.1 | 80.7 | 83.0 |
| 8 | 88.5 | 88.8 | 90.3 | 91.9 | 90.8 | 88.7 |
| 10 | 94.2 | 95.5 | 95.4 | 96.0 | 95.0 | 95.7 |
| 12 | 97 | 98.7 | 97.6 | 97.5 | 96.7 | 97.1 |

The invention claimed is:

1. Sustained-release morphine sulphate microgranules each comprising a neutral support grain coated with an active layer and with a sustained-release layer, said sustained-release layer containing:
   a copolymer of poly(ethylacrylate, methyl methacrylate, trimethylammonioethyl methacrylate chloride) 1:2:0.1;
   a plasticizer; and
   a lubricant;
   wherein said sustained-release layer further comprises a hydrophobic silica which represents 0.2 to 1% by weight of the microgranules and wherein said microgranules are devoid of any outer protective film.

2. Microgranules according to claim 1, characterized in that the relative mass proportion of the morphine sulphate and of the neutral support grain is between 40/60 and 60/40.

3. Microgranules according to claim 1, characterized in that the morphine sulphate represents 30 to 40% by mass of the microgranules.

4. Process for preparing the microgranules according to claim 1, characterized in that the active layer and the sustained-release layer are applied onto the neutral grains by emplacing in aqueous solution.

5. Pharmaceutical composition containing the microgranules according to claim 1, optionally obtained according to the process for preparing the microgranules, characterized in that the active layer and the sustained-release layer are applied onto the neutral grains by emplacing in aqueous solution.

6. Microgranules according to claim 1, wherein the plasticizer is triethylcitrate.

7. Microgranules according to claim 1, further comprising 30–40% wt neutral support grain.

8. Microgranules according to claim 1, further comprising 10–20% wt binder.

9. Microgranules according to claim 1, further comprising 1–2.5% wt plasticizer.

10. Microgranules according to claim 1, further comprising 2–4% wt lubricant.

11. Microgranules according to claim 1, further comprising 5–15% wt methacrylic acid copolymer.

12. Microgranules according to claim 1, further comprising 30–40% wt morphine sulphate, 30–40% wt neutral support grain, 10–20% wt binder, 1–2.5% wt plasticizer, 2–4% wt lubricant, and 0.2–1% wt hydrophobic silica.

13. Microgranules according to claim 1, characterized in that they have the following composition (% by mass):

| morphine sulphate | 37.3 |
|---|---|
| neutral grains | 37.3 |
| hydroxypropylmethylcellulose | 13.0 |
| poly(ethylacrylate, methyl methacrylate, trimethylammonioethyl methacrylate chloride) 1:2:0.1 | 8.2 |
| triethylcitrate | 1.6 |
| talc and | 2.1 |
| hydrophobic silica | 0.4. |

14. Microgranules according to claim 1, characterized in that they have the following composition (% by mass):

| morphine sulphate | 35.1 |
|---|---|
| neutral grains | 39.7 |
| Hydroxypropylmethylcellulose | 12.3 |
| poly(ethylacrylate, methyl methacrylate, trimethylammonioethyl methacrylate chloride) 1:2:0.1 | 8.2 |
| Triethylcitrate | 1.6 |
| talc and | 2.6 |
| hydrophobic silica | 0.4. |

15. Microgranules according to claim 1, characterized in that they have the following composition (% by mass):

| morphine sulphate | 40.9 |
|---|---|
| neutral grains | 34.3 |
| hydroxypropylmethylcellulose | 14.3 |
| poly(ethylacrylate, methyl methacrylate, trimethylammonioethyl methacrylate chloride) 1:2:0.1 | 6.7 |
| triethylcitrate | 1.3 |
| talc and | 2.2 |
| hydrophobic silica | 0.3. |

16. Microgranules according to claim 1, characterized in that they have the following composition (% by mass):

| morphine sulphate | 41.9 |
|---|---|
| neutral grains | 33.0 |
| Hydroxypropylmethylcellulose | 11.7 |
| PEG 4000 | 2.9 |
| poly(ethylacrylate, methyl methacrylate, trimethylammonioethyl methacrylate chloride) 1:2:0.1 | 7.3 |
| Triethylcitrate | 1.4 |
| Talc | 1.4 |
| hydrophobic silica | 0.4. |

* * * * *